(12) United States Patent
McKernan et al.

(10) Patent No.: US 6,283,948 B1
(45) Date of Patent: Sep. 4, 2001

(54) TROCAR OBTURATOR HAVING GROOVED PASSAGEWAY

(75) Inventors: Daniel J. McKernan, Sylvania, OH (US); Gene W. Kammerer, East Brunswick; Keith Seritella, Kendall Park, both of NJ (US); Joan M. Sullivan, Hanover, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/351,649

(22) Filed: Jul. 13, 1999

(51) Int. Cl.[7] .................................................. A61M 5/32
(52) U.S. Cl. .............................................................. 604/272
(58) Field of Search ................................... 604/158–162, 604/272; 606/160, 161, 162, 164, 167, 170, 171, 185

(56) References Cited

U.S. PATENT DOCUMENTS

| 2,541,542 | * | 2/1951 | Perez et al. | 606/167 |
|---|---|---|---|---|
| 3,039,468 | * | 7/1962 | Price | 606/167 |
| 5,279,553 | | 1/1994 | Winkler et al. . | |
| 5,360,416 | | 11/1994 | Ausherman et al. . | |
| 5,651,790 | | 7/1997 | Resnick et al. . | |
| 5,667,514 | | 9/1997 | Heller . | |
| 5,779,624 | * | 7/1998 | Chang | 600/114 |
| 5,853,391 | | 12/1998 | Bell . | |
| 5,908,431 | * | 6/1999 | Battenfield | 606/167 |

\* cited by examiner

Primary Examiner—Manuel Mendez
(74) Attorney, Agent, or Firm—Emil Richard Skula

(57) ABSTRACT

An obturator for use in surgical procedures, particularly minimally invasive procedures. The obturator has an elongated member having a distal piercing tip. The obturator also has a longitudinal groove for containing a surgical instrument for insertion into a body space.

25 Claims, 7 Drawing Sheets

TROCAR OBTURATOR HAVING GROOVED PASSAGEWAY

TECHNICAL FIELD

The field of art to which this invention relates is surgical instrumentation for minimally invasive procedures, in particular, trocar obturators.

BACKGROUND OF THE INVENTION

Obturators are devices that are well known in the minimally invasive surgical arts. Typically an obturator is used to surgically make a small entryway or passageway into a body cavity or a joint. Quite often obturators are mounted coaxially into cannulas. The combined obturator and cannula combination is inserted into the body cavity or joint, and then the obturator is removed; thereby providing a passageway into the body cavity or joint for use in a minimally invasive surgical procedure. Quite often, several cannulas are utilized since a minimally invasive procedure requires at least one cannula or entryway for a camera or other remote viewing device.

Although the obturators and obturator-cannula combinations known in the art perform their function in a satisfactory manner, there is need in this art for new obturators which can be used without a cannula to provide an entryway into a body cavity or joint.

DISCLOSURE OF THE INVENTION

Accordingly, it is an object of the present invention to provide an obturator that can be used to introduce a surgical instrument into a body cavity or joint.

Therefore an obturator is disclosed. The obturator has an elongated member having a distal end, a proximal end, a longitudinal axis and an outer surface. A groove extends into the member through the outer surface. The groove is substantially parallel to the longitudinal axis of the elongated member. The groove has a proximal end, a distal end, a bottom and an open top. The distal end of the groove is ramped up from the bottom of the groove to the outer surface of the elongated member. A piercing point extends from the distal end of the elongated member. An optional handle extends from the proximal end of the member.

Yet another aspect of the present invention is a method of using the above-described obturator of the present invention in a surgical procedure.

These and other aspects of the present invention will become more apparent by the following description and accompanying drawings.

DESCRIPTION OF THE PREFERRED EMBODIMENTS

Figure 1:
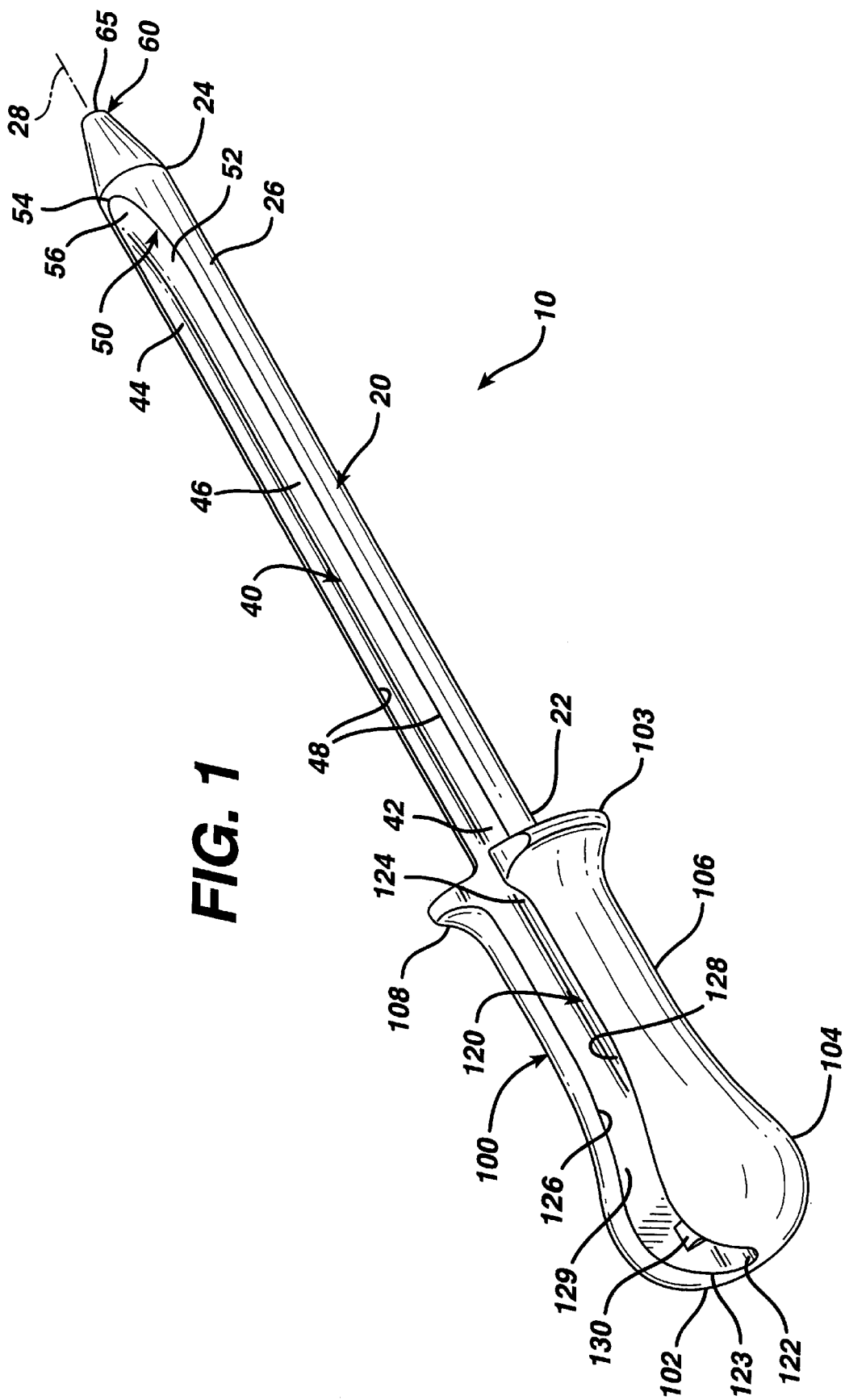
FIG. 1 is a perspective view of an obturator of the present invention.
Figure 2:
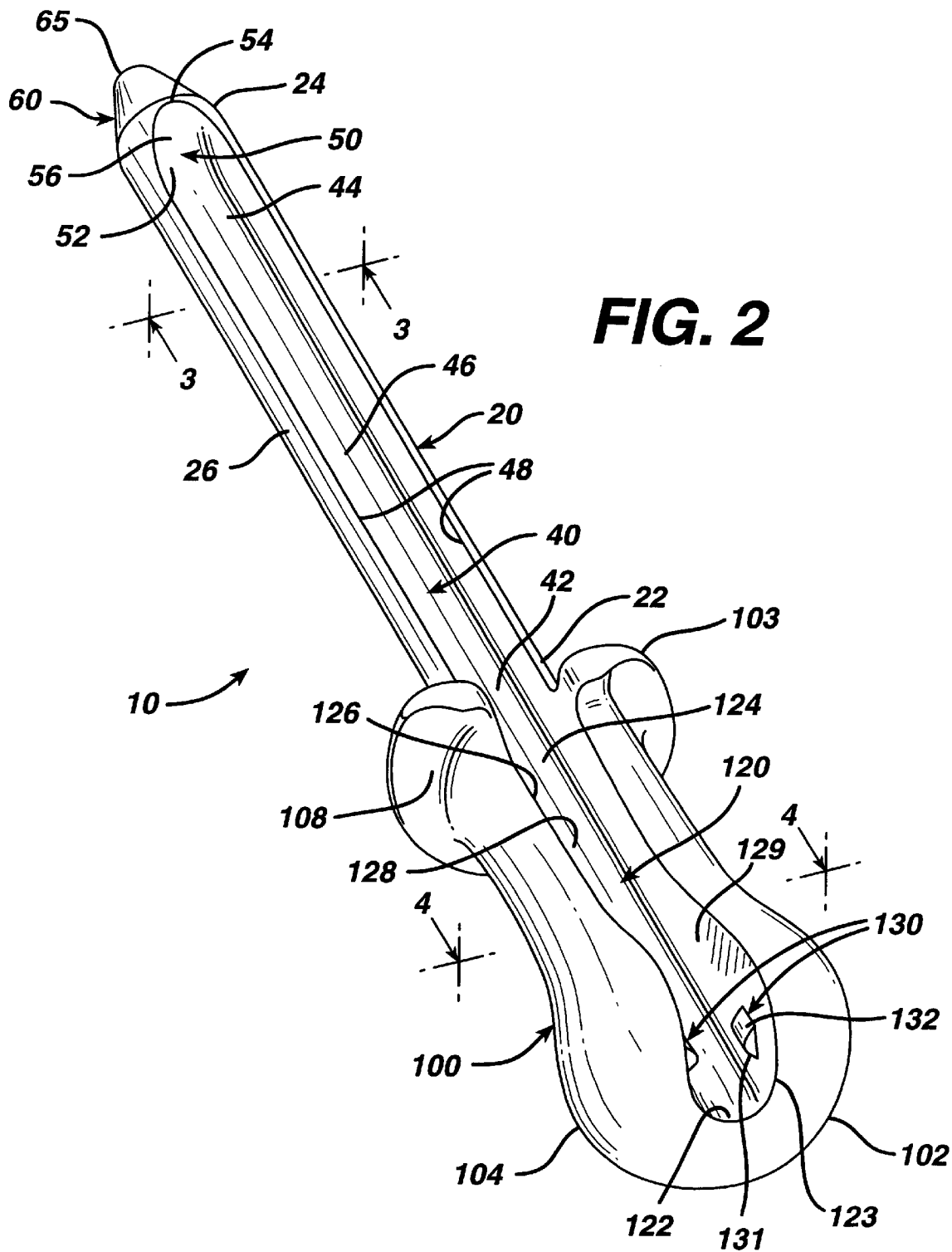
FIG. 2 is yet another perspective view of an obturator of the present invention illustrating the groove in the obturator.
Figure 3:
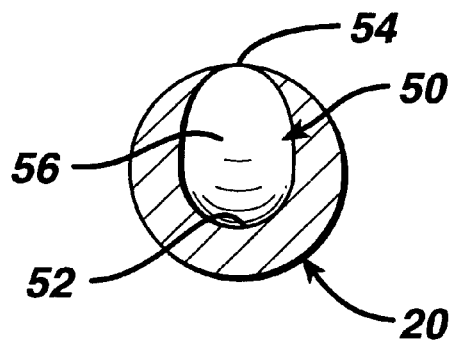
FIG. 3 is a cross-sectional view of the obturator of FIGS. 1 and 2 along view line 3—3.
Figure 4:
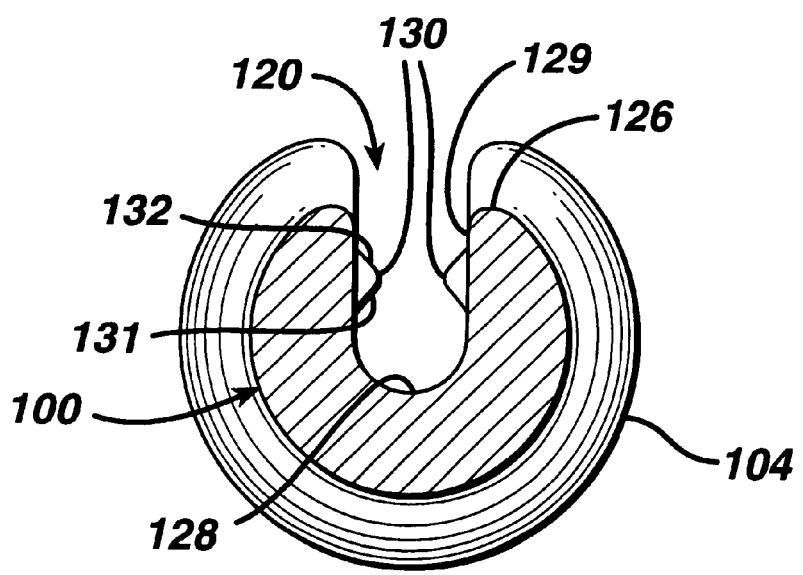
FIG. 4 is a cross-sectional view of the obturator of FIGS. 1 and 2 along view line 4—4.
Figure 10:
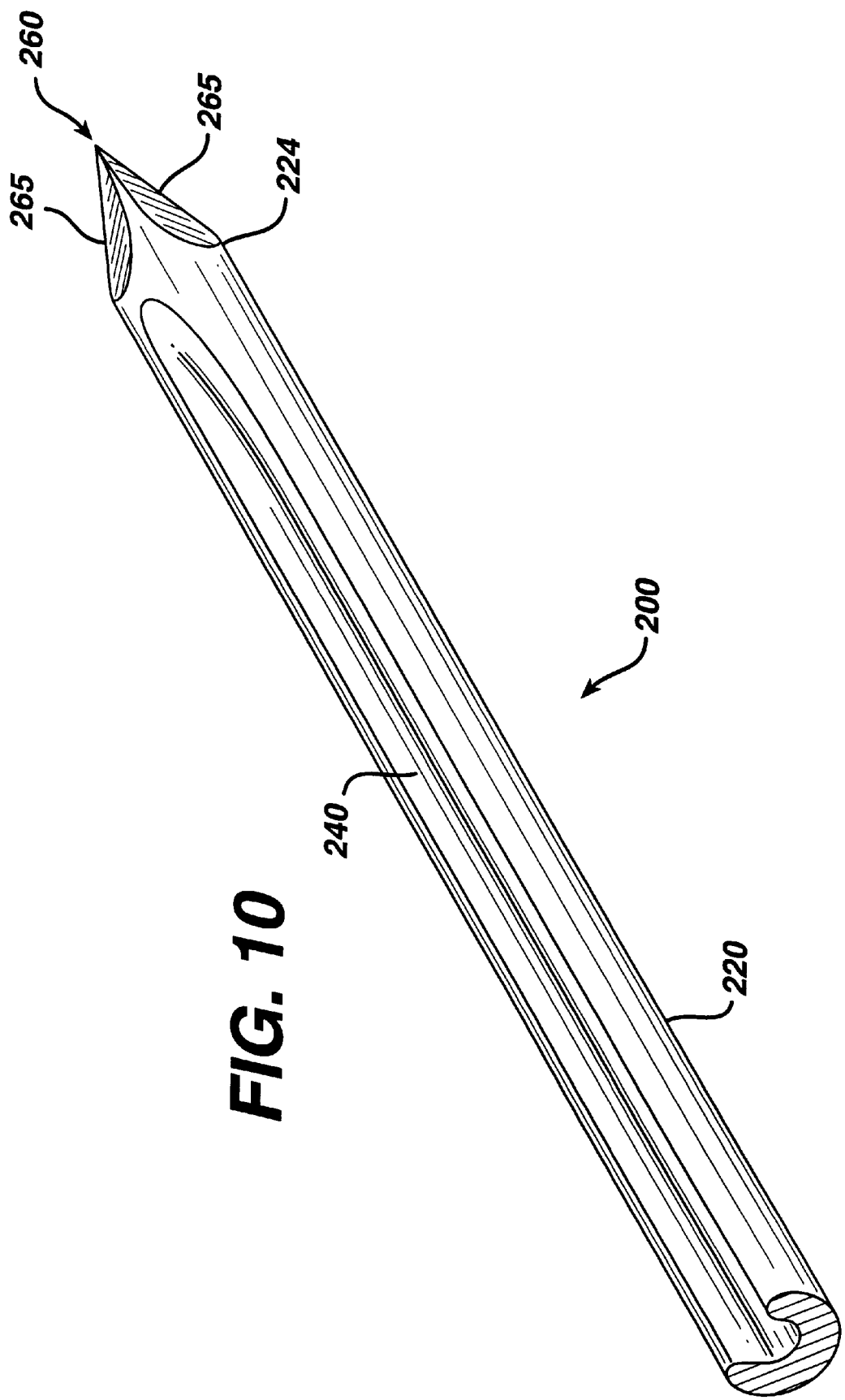
FIG. 10 illustrates an alternative embodiment of an obturator of the present invention wherein the obturator has a pointed distal end and sharp cutting edges.

Referring to FIGS. 1–4, an obturator of the present invention is illustrated. The obturator 10 is seen to have elongated member 20. Elongated member 20 is seen to have proximal end 22, distal end 24, outer surface 26, and longitudinal axis 28. Extending distally from the proximal end 22 of the elongated member 20 is the tip 60. Tip 60 is seen to have point 65. The tip 60 and point 65 may be blunt as shown in FIGS. 1–4, or may be sharp and piercing with cutting edges as seen in FIG. 10. The elongated member 20 is seen to have preferably a circular cross-section as seen in FIG. 3. However, other geometric cross-sections may be utilized including square, rectangular, polygonal, triangular, elliptical curve, combinations thereof and the like. Extending proximally from the proximal end 22 of the member 20 is the handle 100. Handle 100 is seen to have proximal end 102 and distal end 103. Adjacent to the end 102 is the expanded gripping section 104 that tapers down to the narrow section 106. Distal to the narrow section 106 and adjacent to proximal end 103 is the rim member 108.

Contained in the elongated member 20 is the instrument receiving groove 40. Groove 40 is seen to have proximal end 42, distal end 44 and bottom 46. In addition, the groove is seen to have open top 48. Adjacent to the distal end 44 of the groove 40 is the ramped structure 50 which has bottom end 52 adjacent to the bottom 46 of groove 40 and top end 54 adjacent to the outer surface 26, and ramp surface 56 between ends 52 and 54. Although not preferred, the ramp structure 50 may be optionally removed from the groove 40. Extending through the handle 100 and communicating with the groove 40 is the groove 120. Groove 120 is seen to have distal end 124, proximal end 122, opening 123 in handle 100 in communication with groove 120, top opening 126, bottom 128 and sides 129. Extending inwardly from the sides 129 of groove 120 in the area of enlarged section 104 are the optional retention members 130. The retention members 130 are seen to have bottoms 131 and tops 132. The members 130 are seen to have a curved cross-sectional configuration, but may have any geometrical configuration including triangular, semi-circular, polygonal, rectangular, square, combinations thereof and the like.

An alternate embodiment of the obturator 10 of the present invention is seen in FIG. 10. In FIG. 10, the obturator 200 is seen to have a substantially elongated member 220 having a groove 240 (the handle is not illustrated in this figure). The obturator 210 is seen to have a sharp cutting distal point 260 extending proximally from the end 224 of the member 220, and a plurality of cutting edges 265 adjacent thereto.

Figure 5:
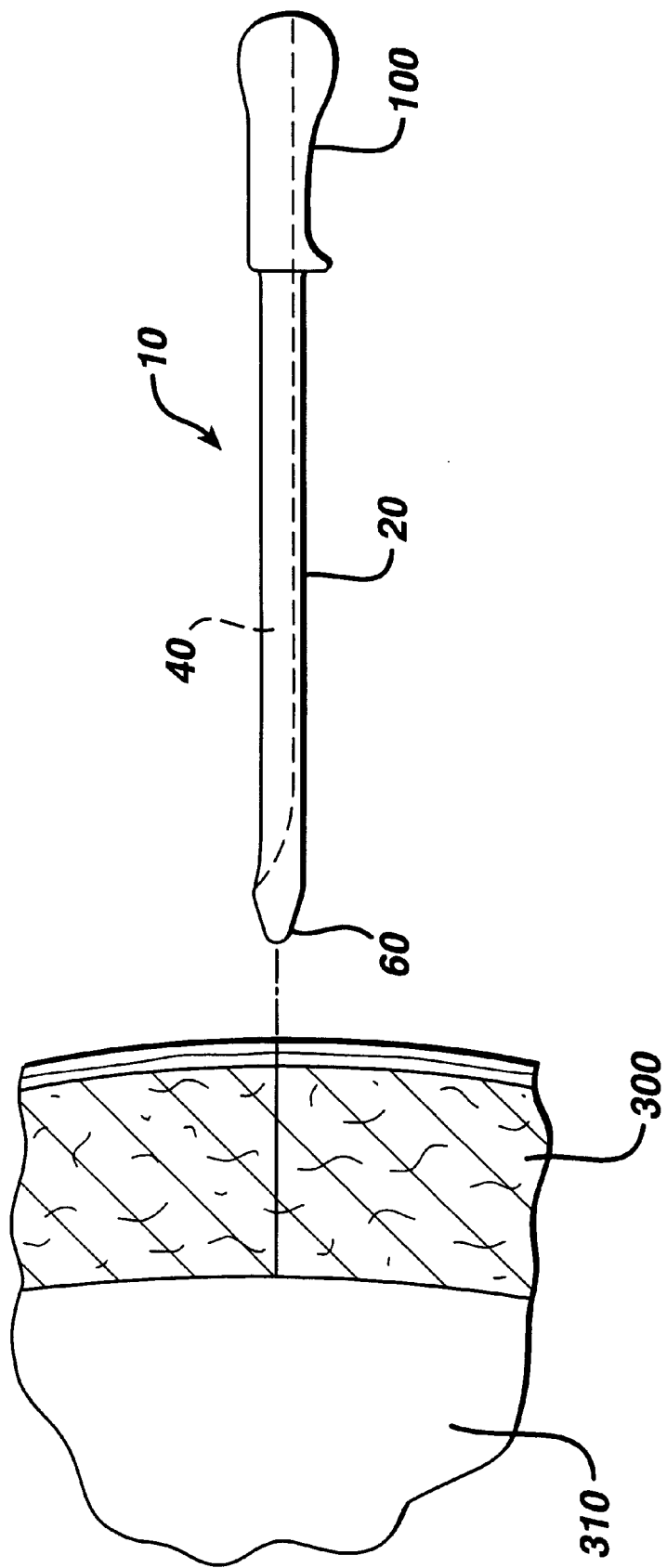
FIGS. 5–7 illustrate the use of the obturator of the present invention to insert a surgical instrument through a body wall into a body space wherein the surgical instrument is inserted into the body space subsequent to the insertion of the obturator.
Figure 6:
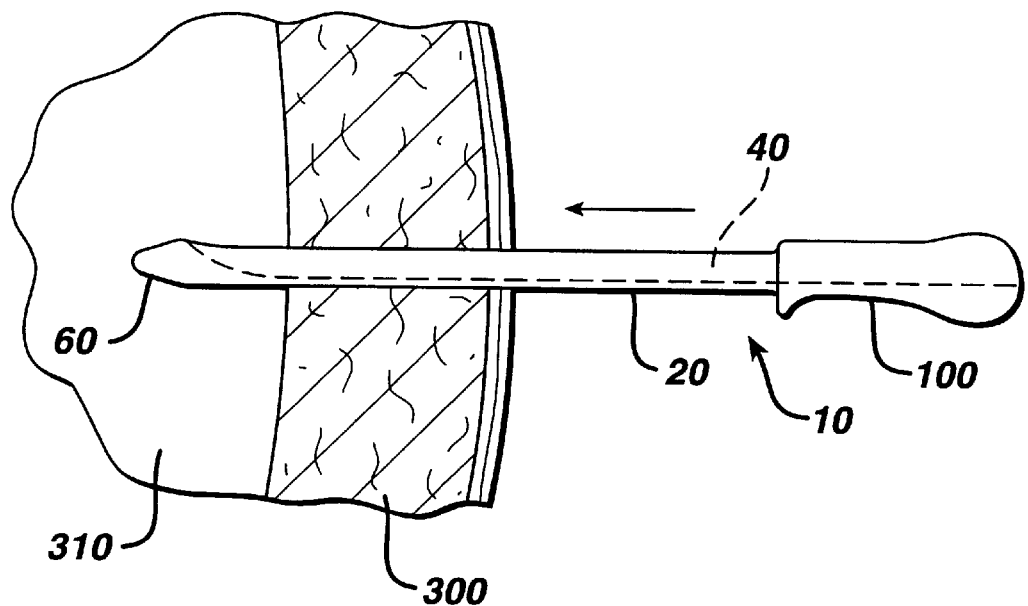
Figure 7:
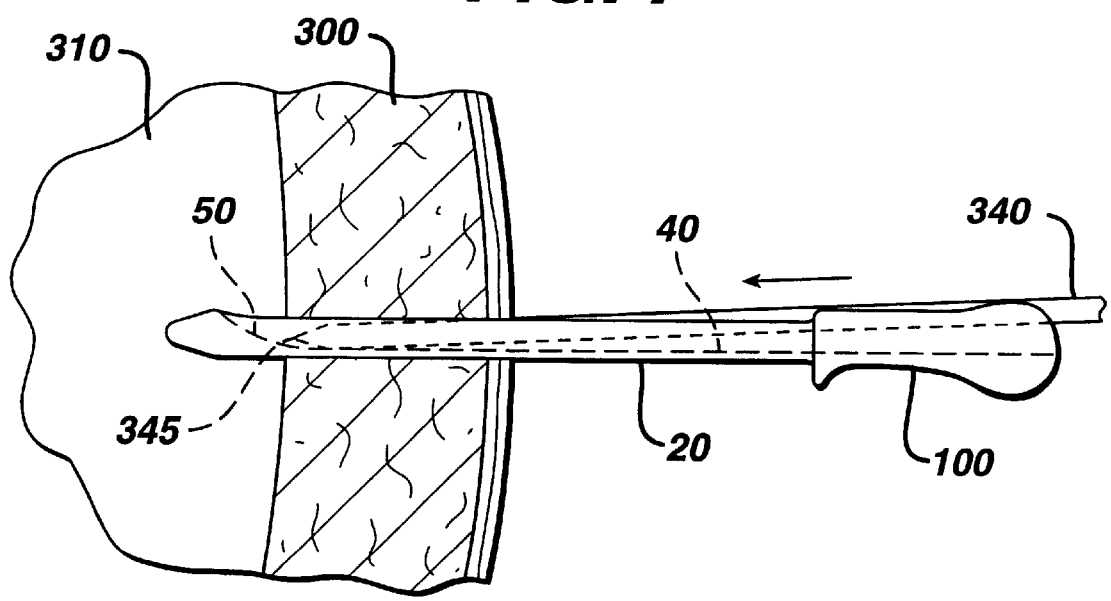

Referring now to FIGS. 5–7, it can been seen that the obturator 10 of the present invention is utilized in the following manner to perform surgical procedures, including minimally invasive procedures. The obturator 10 is inserted through body wall 300 into body space 310. If the procedure is minimally invasive, the body cavity will be viewed by a conventional remote scope device, and will be preferably insufflated with a conventionally used optically clear fluid such as saline, carbon dioxide and the like. Prior to insertion, a surgical insertion is preferably made in the body wall 300, although this is not required in every procedure. Body space 310 may be a body cavity such as the abdominal cavity, or space 310 maybe a joint, such as the knee joint. After the distal point 60 penetrates through body wall 310 such that a significant portion of the distal end of the member 20 is contained within the body space 310, a surgical instrument 340 is then inserted into opening 123 and moved distally through groove 120 and groove 40 and moved distally such that the distal end 345 of the instrument 340 moves through the groove 40 and exits the groove 40 into the body space 310 adjacent to the ramp 50. The obturator 10 may then either be withdrawn from the body space or maintained in the body space providing a pathway into and out of the body space through the body wall 300.

Figure 8:
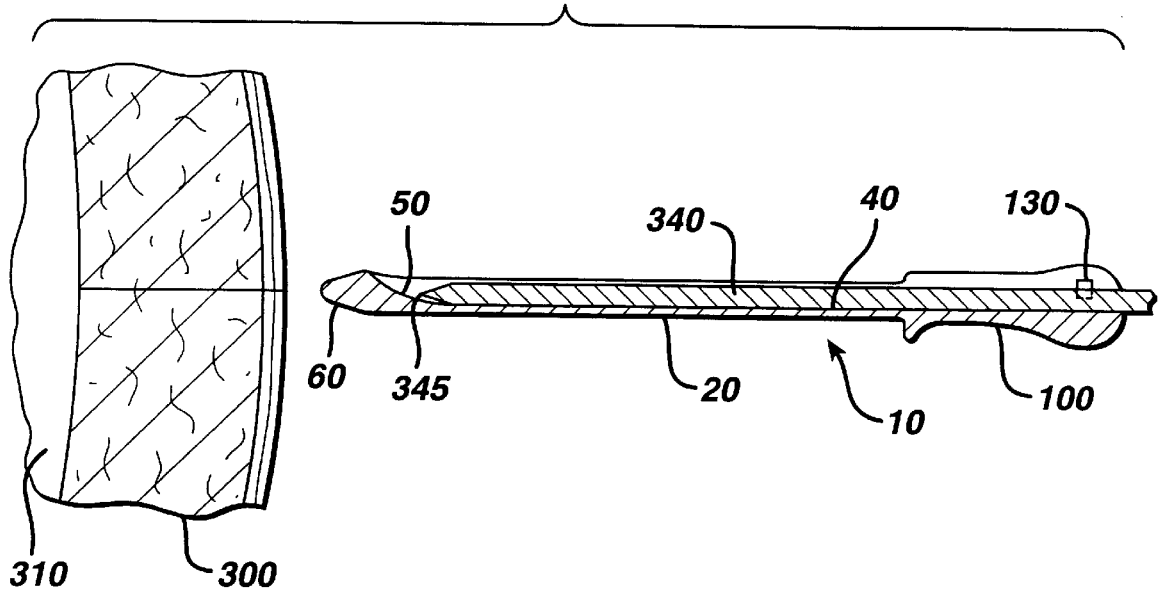
FIGS. 8–9 illustrate the use of the obturator of the present invention to insert a surgical instrument through a body wall into a body space wherein the surgical instrument is inserted into the body space simultaneous with the insertion of the obturator.
Figure 9:
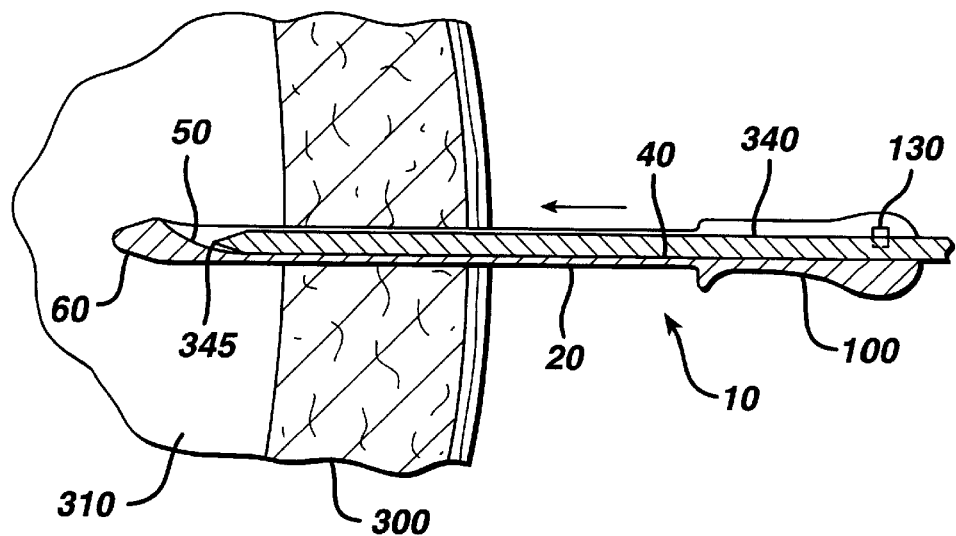

A variation of this procedure using the obturator 10 of the present invention is illustrated in FIGS. 8 and 9. In this variation, the surgical instrument 340 is maintained in the grooves 120 and 40 of the obturator 10 prior to insertion through the body wall 300. The instrument 340 is frictionally engaged while in grooves 120 and 40 by the optional retention members 130. Then, both the obturator 10 and the surgical instrument 340 contained in the grooves 120 and 40 are inserted through the body wall 300 and into the body space 310. The instrument 340 is then manipulated as previously described above.

As mentioned previously, an alternate way of using the grooved obturator 10 of the present invention is to insert the distal tip 60 of the elongated member 20 directly through the body wall into the body space without previously making a surgical incision. Depending upon the type of tissue in the body wall and its thickness, it may be necessary to use an obturator 200 as seen in FIG. 10 having a pointed piercing tip 260 and optional cutting edges 265.

Although this invention has been shown and described with respect to detailed embodiments thereof, it will be understood by those skilled in the art that various changes in form and detail thereof may be made without department from the spirit and scope of the claimed invention.

We claim:

1. An obturator, comprising
a solid rod having a distal end, a proximal end, a longitudinal axis and an outer surface;
a groove extending partially into the rod through the outer surface, said groove substantially parallel to the longitudinal axis, said groove having a proximal end, a distal end proximal to the distal end of the rod, a closed bottom, opposed sides, a width between the sides and an open top having a width, wherein the width of the opening of the top is greater than or equal to the width between the sides; and,
a piercing point extending distally from the distal end of the rod,
wherein an elongated instrument contained within the groove is displaceable radially outward from the groove.

2. The obturator of claim 1, further comprising a handle mounted to the proximal end.

3. The obturator of claim 1, wherein the piercing point is sharp.

4. The obturator of claim 3, wherein the piercing point additionally comprises cutting edges.

5. The obturator of claim 1, wherein the piercing point is blunt.

6. The obturator of claim 2 wherein the groove extends through the handle.

7. The obturator of claim 2 having a pair of opposed projections extending out from the sides of the groove in the handle for retaining a surgical instrument.

8. A method of performing a surgical procedure, comprising:
providing an obturator comprising:
a solid rod having a distal end, a proximal end, a longitudinal axis and an outer surface;
a groove extending partially into the rod through the outer surface, said groove substantially parallel to the longitudinal axis, said groove having a proximal end, a distal end proximal to the distal end of the rod, a closed bottom, opposed sides, a width between the sides and an open top having a width wherein the width of the opening of the top is greater than or equal to the width between the sides; and,
a piercing point extending distally from the distal end of the rod;
inserting the distal end of the obturator through a body wall and into a body space;
introducing an elongated surgical instrument into the body space by sliding the instrument through the groove in the obturator into the body space; and,
displacing the instrument radially outward from the groove into the body space.

9. The obturator of claim 8, further comprising a handle mounted to the proximal end.

10. The obturator of claim 8, in the piercing point is sharp.

11. The obturator of claim 10 wherein the piercing point additionally comprises cutting edges.

12. The obturator of claim 8, wherein the piercing point is blunt.

13. The obturator of claim 9 wherein the groove extends through the handle.

14. The obturator of claim 9 having a pair of opposed projections extending out from the sides of the groove in the handle for retaining a surgical instrument.

15. The method of claim 8 additionally comprising the step of removing the obturator from the body space after the surgical instrument is in place in the body space.

16. A method of performing a surgical procedure, comprising:
providing an obturator comprising:
a solid rod having a distal end, a proximal end, a longitudinal axis and an outer surface;
a groove extending partially into the rod through the outer surface, said groove substantially parallel to the longitudinal axis, said groove having a proximal end, a distal end that is proximal to the distal end of the rod, a closed bottom, opposed sides, a width between the sides and an open top having a widty wherein the width of the opening of the top is greater than or equal to the width between the sides; and,
a piercing point extending distally from the distal end of the rod;
providing an elongated surgical instrument having a distal end;
mounting the distal end of the surgical instrument in the groove of the obturator;
simultaneously inserting the distal end of the obturator and the distal end of the surgical instrument contained within the groove through a body wall and into a body space; and,
displacing the instrument radially outward from the groove into the body space.

17. The obturator of claim 16, further comprising a handle mounted to the proximal end.

18. The obturator of claim 16, wherein the piercing point is sharp.

19. The obturator of claim 18 wherein the piercing point additionally comprises cutting edges.

20. The obturator of claim 16, wherein the piercing point is blunt.

21. The obturator of claim 17 wherein the groove extends through the handle.

22. The obturator of claim 21 having a pair of opposed projections extending out from the sides of the groove in the handle for retaining a surgical instrument.

23. The method of claim 16 additionally comprising the step of removing the obturator from the body space after the surgical instrument is in place in the body space.

24. The surgical method of claim 8, wherein the method is minimally invasive.

25. The surgical method of claim 16, wherein the method is minimally invasive.

\* \* \* \* \*